(12) United States Patent
Buelow et al.

(10) Patent No.: US 10,692,213 B2
(45) Date of Patent: Jun. 23, 2020

(54) RETRIEVAL OF CORRESPONDING STRUCTURES IN PAIRS OF MEDICAL IMAGES

(71) Applicant: KONINKLIJKE PHILIPS N.V., Eindhoven (NL)

(72) Inventors: Thomas Buelow, Grosshansdorf (DE); Klaus Erhard, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 223 days.

(21) Appl. No.: 15/551,776

(22) PCT Filed: Mar. 10, 2016

(86) PCT No.: PCT/EP2016/055194
§ 371 (c)(1),
(2) Date: Aug. 17, 2017

(87) PCT Pub. No.: WO2016/142492
PCT Pub. Date: Sep. 15, 2016

(65) Prior Publication Data
US 2018/0033143 A1 Feb. 1, 2018

(30) Foreign Application Priority Data

Mar. 10, 2015 (EP) .................................... 15158342

(51) Int. Cl.
*G06K 9/00* (2006.01)
*G06T 7/00* (2017.01)
(Continued)

(52) U.S. Cl.
CPC ............ *G06T 7/0014* (2013.01); *A61B 6/025* (2013.01); *A61B 6/4241* (2013.01); *A61B 6/463* (2013.01);
(Continued)

(58) Field of Classification Search
None
See application file for complete search history.

(56) References Cited

U.S. PATENT DOCUMENTS

2003/0007598 A1 1/2003 Wang
2003/0194121 A1 10/2003 Eberhard
(Continued)

FOREIGN PATENT DOCUMENTS

WO 9621199 7/1996
WO 2004095378 11/2004
(Continued)

OTHER PUBLICATIONS

Torabi, et al., "Local self-similarity-based registration of human ROIs in pairs of stereo thermal-visible videos", Pattern Recognition, vol. 46, No. 2, Feb. 1, 2013.
(Continued)

*Primary Examiner* — Atiba O Fitzpatrick
(74) *Attorney, Agent, or Firm* — Larry Liberchuk

(57) ABSTRACT

A system and related method for retrieving, for a first image structure (S1) in an initial image (IG1), a corresponding image structure (S2) in a second image (IG2). The system accepts as input a location of the first structure (S1) in the initial image (IG1) along with an additional structure property such as spectral information to so reduce ambiguity.

17 Claims, 3 Drawing Sheets

(51) Int. Cl.
    *A61B 6/02*  (2006.01)
    *A61B 6/00*  (2006.01)
    *G06T 7/73*  (2017.01)
    *G06K 9/20*  (2006.01)
    *G06K 9/62*  (2006.01)
    *G06T 7/60*  (2017.01)

(52) U.S. Cl.
    CPC .............. *A61B 6/469* (2013.01); *A61B 6/502* (2013.01); *A61B 6/5217* (2013.01); *A61B 6/5235* (2013.01); *G06K 9/2081* (2013.01); *G06K 9/6203* (2013.01); *G06K 9/6215* (2013.01); *G06T 7/60* (2013.01); *G06T 7/74* (2017.01); *A61B 6/482* (2013.01); *A61B 6/5223* (2013.01); *G06K 2209/05* (2013.01); *G06T 2200/24* (2013.01); *G06T 2207/10024* (2013.01); *G06T 2207/10081* (2013.01); *G06T 2207/10088* (2013.01); *G06T 2207/10112* (2013.01); *G06T 2207/30068* (2013.01); *G06T 2207/30096* (2013.01)

(56) References Cited

U.S. PATENT DOCUMENTS

| | | | |
|---|---|---|---|
| 2006/0067473 A1* | 3/2006 | Eberhard | ............... A61B 6/025 378/98.9 |
| 2007/0297662 A1 | 12/2007 | Marzendorfer | |
| 2008/0144767 A1 | 6/2008 | Eberhard | |
| 2009/0034684 A1 | 2/2009 | Bernard | |
| 2010/0195882 A1 | 8/2010 | Ren | |
| 2010/0286517 A1 | 11/2010 | Kamen | |
| 2011/0058724 A1 | 3/2011 | Claus | |
| 2011/0123073 A1 | 5/2011 | Gustafson | |
| 2014/0321607 A1 | 10/2014 | Smith | |
| 2016/0235380 A1* | 8/2016 | Smith | ................... A61B 6/025 |
| 2018/0033143 A1 | 2/2018 | Buelow | |

FOREIGN PATENT DOCUMENTS

| | | |
|---|---|---|
| WO | 2013/035026 | 3/2013 |
| WO | 2013078476 | 5/2013 |
| WO | 2014206881 | 12/2014 |

OTHER PUBLICATIONS

Ehrhardt, et al., "Automatic correspondence detection in mammogram and breast tomosynthesis images", Proceeding of SPIE, vol. 8314, Feb. 10, 2012.

Chan, et al., "Computer-aided detection of masses in digital tomosynthesis mammography: Comparison of three approaches", Medical Physics, vol. 35, No. 9, Aug. 14, 2008.

Froeling, et al., "Correlation of contrast agent kinetics between iodinated contrast-enhanced spectral tomosynthesis and gadolinium-enhanced MRI of breast lesions", European Radiology, vol. 23, No. 6, Jan. 10, 2013.

Selby, et al., "Reconstruction and registration of multispectral x-ray images for reliable alignment correction in radiation treatment devices", Optical Sensing II, vol. 6914, Mar. 6, 2008.

Alvarez et al "Energy-selective reconstruction in X-ray Computerized Tomography" in Phys Med Biol, vol. 21, No. 5, pp. 733-744 (1976).

* cited by examiner

RETRIEVAL OF CORRESPONDING STRUCTURES IN PAIRS OF MEDICAL IMAGES

CROSS REFERENCE TO RELATED APPLICATIONS

This application is the U.S. National Phase application under 35 U.S.C. § 371 of International Application No. PCT/EP2016/055194, filed Mar. 10, 2016, published as WO 2016/142492 on Sep. 15, 2016, which claims the benefit of European Patent Application Number 15158342.4 filed Mar. 10, 2015. These applications are hereby incorporated by reference herein.

FIELD OF THE INVENTION

The invention relates to an image processing system, to an image processing method, to computer program element, and to a computer readable medium.

BACKGROUND OF THE INVENTION

In medicine or other fields of interest there may be a need to identify corresponding structures in a plurality of images. In medicine, this task may come up in analyzing images from prior versus follow-up examinations or in analyzing multimodal imagery.

A more specific example where this task frequently occurs is digital breast tomosynthesis (DBT). DBT is an emerging technology in breast imaging where a series of high resolution images of the breast is produced by limited angle tomography. Compared to conventional 2D digital radiography, the amount of image data to be reviewed is significantly higher for "2.5D" tomosynthesis data. Efficient tools for reading and analysis of the tomosynthesis data is therefore desirable, especially in a breast screening setting. To this end, synthetic mammograms have been recently proposed to support efficient reading of tomosynthesis data by an interactive slice selection technique as in Applicant's WO 2013/035026.

Still, finding corresponding image structures can be at times challenging for reasons other than sheer data volume. For instance, in diagnostic breast imaging it may be difficult to identify corresponding lesions acquired at different views such as ipsi-lateral mammographic views taken in the standard cranio-caudal (CC) and medio-lateral oblique (MLO) orientations. Another difficulty in dealing with such multi-view imagery may arise if one wishes to navigate to a certain tomosynthesis slice which one expects to depict more clearly a structure of interest as seen, eg, in a currently displayed synthetic mammogram.

SUMMARY OF THE INVENTION

There may therefore be a need for an image processing systems and/or method to support navigation or structure-finding tasks across a plurality of images.

The object of the present invention is solved by the subject matter of the independent claims where further embodiments are incorporated in the dependent claims. It should be noted that the following described aspect of the invention equally apply to the image processing method, to the computer program element and to the computer readable medium.

According to a first aspect of the invention there is provided an image processing system comprising:

an input port configured to receive, for a first image of an object, an input specification comprising: i) a location for a first image structure in said first image and ii) a structure property that relates to a corresponding physical property of at least a part of said object;

an image structure retriever configured to identify, based on said input specification, a second image structure in a second image;

a graphics display generator configured to display on a display device said second image structure, wherein the structure property specification includes at least spectral information.

In other words, the proposed system is configured a cross-image search and retrieve operation to help user navigate efficiently across potentially complex and rich imagery representing different views of a region of interest.

The proposed system allows linking information from the two images together. In particular the link can be attempted for any second image given the first image. The link is established for instance first time upon carrying out the identification operation. No prior knowledge about the particular second image to be linked to is required for the proposed method although such knowledge is not excluded. Also, the proposed system does not merely link the image structure/portion of the first image to the second image, but does link to a corresponding structure within the second image.

The first and second image are of the same object or part thereof and the second image structure corresponds to the first image structure, that is, the two structures represent each the same object or part in the (at least) two images.

According to one embodiment, the image structure retriever's identification operation includes comparing the first and second image structures based on a similarity measure.

According to one embodiment, the similarity measure includes any one or a combination of: grey value histogram similarity, similarity in spectral or material composition, similarity in any one of size, morphology, texture, contrast uptake.

According to one embodiment, the structure property specification includes any one or a combination of: i) a size and/or shape parameter, ii) material type parameter.

According to one embodiment, the image structure retriever's identification operation includes propagating a shape from the first into the second image, said shape being specified by the, or a, shape parameter.

According to one embodiment, the object is repositioned and/or deformed between respective acquisitions by an imager of the first and second image.

According to one embodiment, the first and the second image furnish different views of the object, the first and second image structures being representative of a part of interest of or in said object.

According to one embodiment, the first image is a 2D or a 3D image and wherein the second image is a 2D or 3D image.

According to one embodiment, the first and the second images are 3D.

According to one embodiment, the first image or the second image is a synthetic mammogram.

According to one embodiment, the second image and/or the first image is a 3D tomosynthesis volume.

According to one embodiment, the identification operation of the retriever includes identifying a shape/location of the second structure in the second image, that is, the structure of interest in the second image.

According to one embodiment, the image structure retriever's identification operation includes identifying a search region within the second image for application of the similarity measure to image information within said search region.

According to one embodiment, the graphics display generator is configured to effect displaying the first image structure and the second image structure together on the display device.

According to one embodiment, the system comprises a structure analyzer configured to compute a common structure property for said first and second structures. For instance, in one embodiment the common structure property is computed based on the similarity measure. In one embodiment, common structural analysis includes segmenting the two corresponding image structures in their respective images. The common structural property (or properties) such as volume, spectral composition, and material decomposition can then be computed from the segmented structures. The computation can be done in manifold ways, such as by fitting a generic (eg, geometric shape) model to the two segmented structures to "explain" the two structures as features of the model. In one embodiment the graphics display generator operates to display a representation of the common structure property for said first and second structures.

According to one embodiment, the system includes an interactive user interface operable by a user to supply said input specification whilst the first image is being displayed on the display device.

According to one embodiment, the image structure retriever's identification operation includes performing an optimization or search algorithm in respect of the similarity measure, said algorithm and/or similarity measure being selected based on the received input specification.

According to one embodiment, the first and/or the second images have been acquired by a spectral imager.

Because the proposed system processes "enriched" input information (that includes location+ structure property), it can cope even with adverse conditions as in mammography where the identification of corresponding lesions in ipsilateral mammograms or volumes is encumbered with difficulties because of the varying compression of the breast and/or changing viewing directions, either of which causes subsequent changes in the visual appearance of one and the same lesion. In contrast to these automatic schemes, the present system allows the user to supply additional structure input (that is, input over and above a mere location input) in form of expert knowledge on the structure of interest to be sought out. This additional input then "controls" or influences the retrieval operation for the corresponding second structure in the second image. One layer of complexity in dealing in particular with mammographic or other similar imagery is that sometimes a lesion is only visible in one of the standard CC and MLO views due to overlaying structures in the 2D projection view. Although tomosynthesis imaging has the potential to at least partly resolve overlaying image structures, this comes at the cost of producing considerable amount of data to be reviewed for diagnosis. The proposed method addresses this by providing an at least semi-automatic workflow for identification and analysis of lesions where the additional expert knowledge can be used in the retrieval of the corresponding structure.

The system has proved particularly beneficial on spectral tomosynthesis data and synthetic mammograms derived therefrom where the identification operation includes evaluation of the local lesion composition based on the spectral data. In other words, spectral information is used as said additional (over and above a mere location specification) structure property. To further boost the systems capability to resolve ambiguities caused by superimposed image structures, it is proposed in one embodiment to process a plurality of additional structure properties, for instance morphology together with spectral information or any other combination of suitable structure property data items. In particular the proposed method allows coping with the challenging task where the initial ("first") image is a 2D (e.g. a synthetic mammogram) image and the ("second") target image is of higher dimensionality (e.g. "2.5D" such as a tomosynthesis volume or 3D dimensionality) than the initial image as in this 2D→3D scenario the mentioned ambiguity is more pronounced than in scenarios where the identification goes the other way, namely from 3D→2D.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
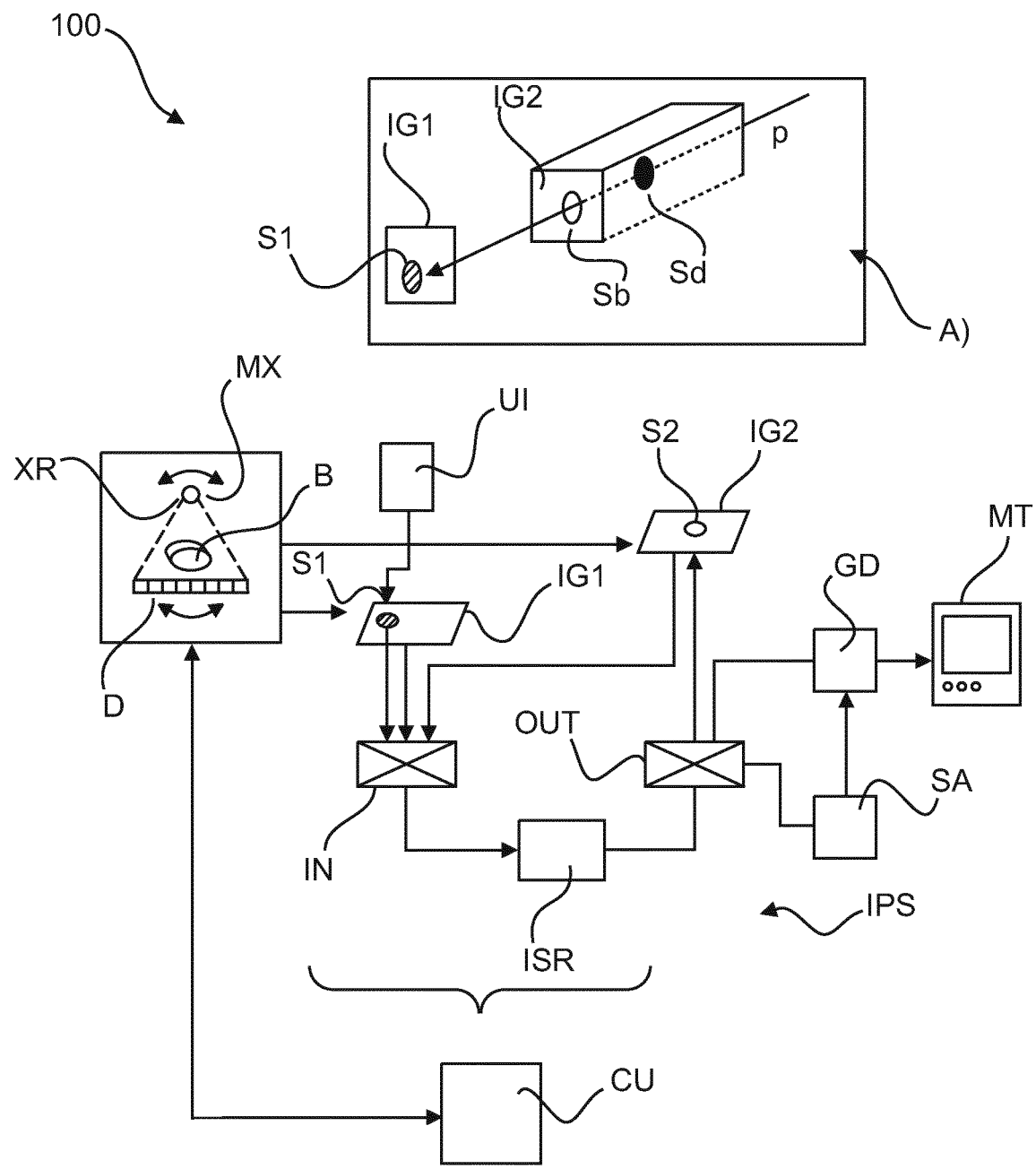
FIG. 1 shows a block diagram of an imaging arrangement.

With reference to FIG. 1, there is shown an imaging arrangement 100. The arrangement 100 comprises an imaging modality MX such as a (3D) tomosynthesis mammography imaging scanner (also referred to herein more generally as the "imager"). Imaging modalities other than mammography imaging scanners are also envisaged herein such as CT (computed tomography) scanners, or MRI imagers, etc.

The mammography scanner MX is configured to obtain images of a female breast. More particularly, the scanner is configured to perform a type of limited-angle tomography known as DTB (digital breast tomosynthesis) or simply tomosynthesis. To do this, the imager MX includes in one embodiment a movable arm (or "gantry") on one, upper end of which is mounted an X-ray source XR and towards the other, lower end an X-ray radiation sensitive detector D.

In use, the X-ray source XR emits X-ray radiation, orbits around the breast B (in a limited arc) and the detector D traces out a correspondingly limited scan arc (about 10-20 degrees) underneath the breast BR whilst the breast is held stationary. In the course of this scan operation a plurality of projection images are acquired by the detector D from signals caused by the X-ray radiation imping on radiation sensitive pixel elements of detector D after passage of said X-ray radiation through the breast tissue. Preferably, the pixel elements are arranged in multiple detector lines so that the projection images capture the full extent (width and breadth) of the breast.

The projection images can be reconstructed by using a tomosynthesis algorithm into a quasi-3D (sometimes called 2.5 dimensional) image volume but referred to herein simply as 3D volume in distinction to 2D projective imagery such as mammograms, on which more later further below. During the acquisition, the breast is compressed in a compression arrangement to enhance image contrast. The scanner MX can be used to acquire projection imagery for different tomosynthesis volumes for different approach angles or views. Common views are "cranio-caudal" (CC) and "medio-lateral-oblique"(MLO), both are usually required for proper diagnostics or check screenings. For each view, the breast may need to be re-positioned and or re-compressed before acquisition of the projection imagery for the next view can commence.

In general then, the image output supplied by the imager MX includes two or more tomosynthesis volumes (e.g. for CC and MLO view). The volumes are organized into component images, so called slices or slabs, each having a certain "thickness". The slices of the volumes are in one embodiment cross-sectional absorption images that reveal the inner structure of the breast which can furnish to the clinicians valuable diagnostic clues. As hinted at earlier, there is also associated 2D imagery derivable from said volumes including synthetic mammograms. These synthetic mammograms are obtained by forward-projections through the respective volumes. Forward-projection is preferably along the directions as per the respective approach angles. These synthetic mammograms afford a more simplified overview image on the respective volumes.

According to one embodiment, the detector D is of the energy integrating type. In an alternative, preferred embodiment, modality MX has spectral imaging capabilities and this can be achieved in some embodiments by using a detector D of the photon counting type.

The arrangement 100 further includes an image processing system IPS. The image processing system IPS as proposed herein helps a user (or an automated protocol) to find or "re-find" corresponding image structures across the imagery produced by the modality MX. Those image structures may represent for instance image footprints of micro classifications whose analysis is of interest in mammography applications. The tomosynthesis volumes represent a considerable amount of image information and manually searching (e.g. "scrolling") through would put too heavy a burden on the ever busy clinicians. To address this, the proposed image processing system IPS allows, in one embodiment, the user to select with a suitable user input means UI an image structure of interest in a first image IG1 and the image processing system then operates to retrieve automatically from a target image IG2 a structure that actually corresponds to the selected structure in the first image IG1. Retrieving the "right" image structure rather than a bogus match may prove difficult and the proposed system IPS addresses this. The reason for this difficulty is ambiguity of imager information. More particularly, Applicants have discovered that the notion of corresponding image structures across images may in itself pose an ambiguity. This is illustrated diagrammatically in inset A) of FIG. 1. For instance, input or initial image IG1 may be a synthetic mammogram obtained through a desired projection p across image volume IG2 schematically shown in inset A) as a cuboid. A certain image structure in the image IG1 of interest S1 is the projection of all image structures across the block IG2 along said projection direction. In other words, structures may overlay to combine into this image structure S1. If the clinician is presented with the mammogram IG1 to visually select image structure S1 as the structure of interest, an ambiguity may arise because it is not clear to the system which one of the overlaying structures is the one that was meant to correspond to S1. Strictly for illustration only, is the bright structure Sb or the dark structure Sd the one that corresponds to structure S1 in initial image IG1? The super-position of image information along the projection directions introduces this ambiguity. A real word example for such a superposition of image structures may occur if, say, a smaller calcification is situated on top or below (in projection direction) a larger mass-lesion.

The image structure selected in the initial image IG1 may be considered as an "index entry" which is used to look up the corresponding structure S2 in the target image IG2. The proposed image processing system IPS affords to the user the capability of defining a "rich" image structure specification in respect of image structure in the initial image to thereby reduce the ambiguity faced by the retrieval operation. The proposed system IPS then uses this rich input specification and its search and retrieve operation in the target volume IG2 can therefore be expected to return, with higher likelihood than for previous systems, the desired, "right" image structure S2.

More particularly, the input specification as proposed herein includes not only a mere location in the initial image IG1 but also additional information that specifies a structural property of the said image structure. It is this "combo" or "dual" nature of the input of the image structure specification that is then used as an input by the image processing system to retrieve a location and/or shape of the corresponding image structure IS2 in the target image IG2.

With continued reference to FIG. 1 there is shown an exemplary architecture of the image processing system IPS which can be thought of as a group of software modules that are run on a computing unit CU such an operating console or a workstation associated with modality MX.

The image processing system IPS includes an input port IN to receive the dual input specification (that is, the location of S1 in image IG1 and the specification of the structure property of said image structure S1 as per the initial IG1). This dual input specification is then forwarded to the image structure retriever ISR that accesses the target image IG2 to operate thereon and to retrieve from therein said corresponding image structure S2. A location and/or shape or extent of the structure S2 in terms of image pixels or voxels say is then output at output port OUT. The structures S1, S2 are said to "correspond" because they represent the respective image footprints (in possibly different views) of the same object (e.g. breast) or a same part thereof. In case of a higher dimensionality target image IG2, the output location of S2 includes in particular its depth within the respective stack of slices. In other words, the proposed identification is in general not merely an identification of the respective structure within one slice (although in some embodiments this may suffice) but in a preferred embodiment the identification operation includes searching across the stack of slices in target image IG2 to precisely pinpoint S2 both according to its depth and in-plane location.

A graphics display generator GD may then cooperate via a suitable visualization module with a display unit MT (such as a monitor) to render for display a representation of structure S2. For instance, this can be achieved by rendering image IG2 on display with a suitable graphical mark-up (e.g. highlighted contour) that shows the retrieved location structure S2.

Operation of the image structure retriever ISR may involve evaluating certain structural properties such as spectral information for instance. The so evaluated information is processed in one embodiment by a structure analyzer SA to compute a common structure property parameter descriptive to both image structures in the images IG1 and IG2. This common structure information can then be displayed alongside the second image IG2 and/or the respective retrieved image structure S2, on monitor MT. For instance, a text box or a graphical UI widget can be phased-in, e.g. can be over-laid on the image IG1 or IG2 for display of the common property in graphical or numerical form.

Figure 2:
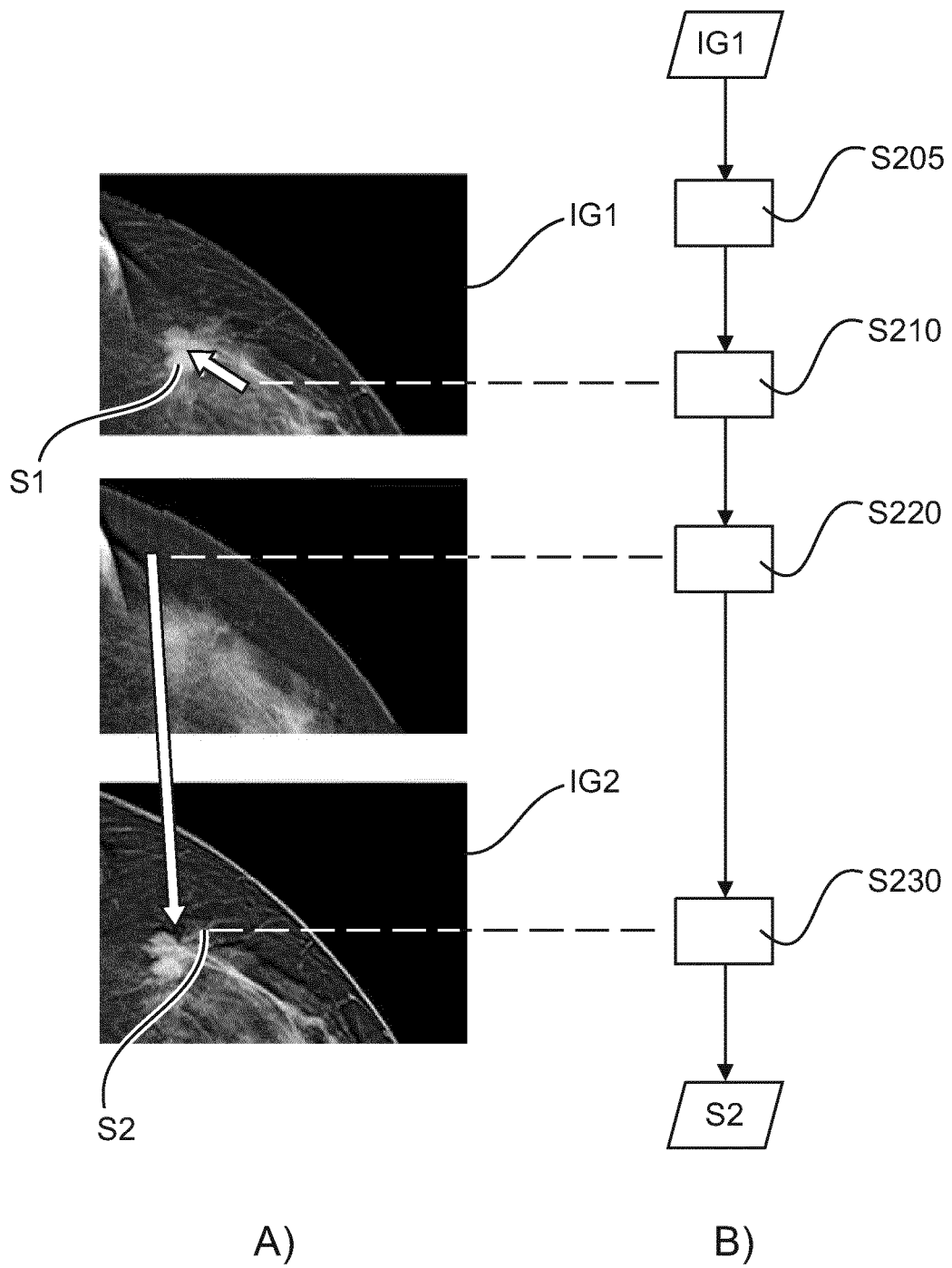
FIG. 2 shows a flow chart with illustrative imagery of an image processing method according to a first embodiment.
Figure 3:
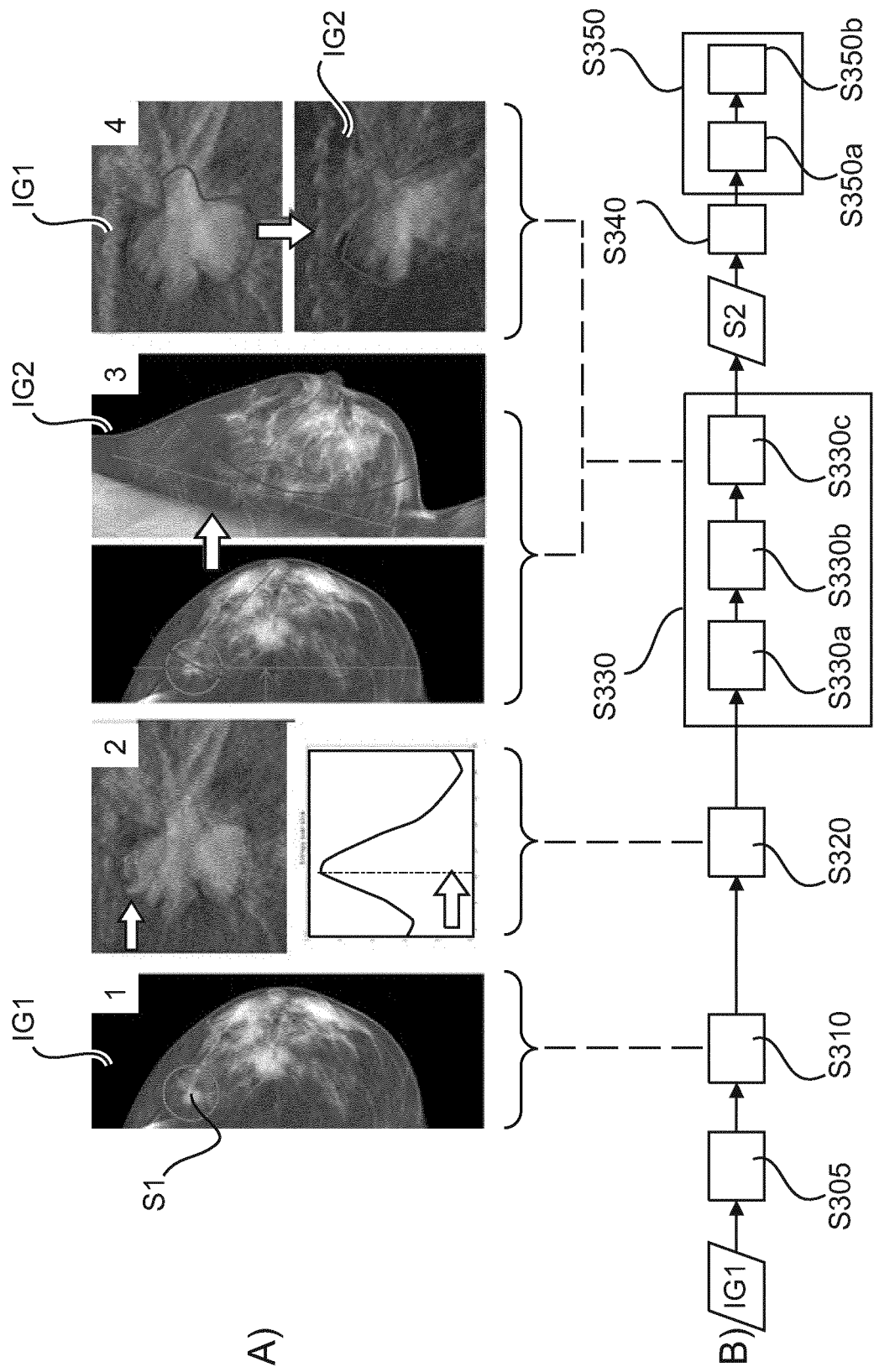
FIG. 3 shows a flow chart with illustrative imagery of an imaging processing method according to a second embodiment.

Reference is now made to FIGS. 2 and 3 which show in their respective parts A) respective flow charts of two embodiments for a method of image processing that explain in more detail the function of the image processing system IPS. Respective parts B) in FIGS. 2,3 include exemplary imagery (that is not to be construed as limiting) to illustrate at least some method steps. It is envisaged herein for the image processing system to be capable of operating according to either one of the two methods in FIG. 2 or 3 or IPS is at least in one embodiment switchable to do so.

Turning now first to flow chart FIG. 2, an embodiment will be described where the input image or initial image IG1 is a synthetic mammogram obtained from a 3D tomosynthesis image volume IG2 and the target image is said volume IG2. However, other image combinations are also envisaged where the target volume is a different image volume. For instance, the synthetic mammogram IG1 is derived from the CC volume and the target volume IG2 is not said CC volume but the image volume for the other (ipsi-lateral) view, namely the MLO volume. However this choice of initial and target image is for illustrative purposes only and any other dimensional combinations for initial and target image are also envisaged herein. For instance, both images IG1, IG2 may be 3D volumes or both are 2D images.

Initially, at step S205, the initial image IG1 (e.g. the synthetic mammogram) is displayed, for instance (this is exemplary only) in a two-pane-view port alongside a default view of the target image IG2. In one embodiment, default view is on a certain slice from the tomosynthesis image volume IG2 that is displayed initially. Alternatively it is only the initial image IG1 that is displayed to the user. However the initial displaying of the initial image IG1 is merely according to one embodiment, as other, automatic embodiments are also envisaged where the step S205 is left out and the method commences at the following step S210.

At step S210, an input specification is received for the initial image IG1. This input specification comprises both, location in the displayed initial image of a structure of interest S1 and a specification of a certain structure property of interest for his structure S1. This structure property relates to a corresponding physical property of a certain part of the object shown in the image. For instance, in mammography the structure may represent a calcification in the female breast. Preferably this "dual" specification is furnished via suitable user interface UI (preferably, but not necessary in all embodiments, as a graphical user interface) components. In one GUI embodiment, the speciation is defined by the user using a suitable pointing device such as a computer mouse that allows the user to select by point-and-click or by pointing-only operation the position of the image structure in the first image IG1. In another, separate, in one embodiment explicit, user action, the additional structure property is specified, eg, by mouse scroll-wheel operation, by drop-down menu selection, list selection, textual input via keyboard, etc. Other input means such as e-stylus, or touch screen action is also envisaged herein. When furnishing this combo information the system is thought to operate in a "ROI selection mode", the selected image structure S1 being within a ROI.

In short, it is proposed herein in one embodiment to allow the user not only to specify the location of the structure of interest but also to provide additional information about the structure of interest S1 in the currently displayed initial image IG1. This additional structural information may comprise for instance a delineation of the structure. A delineation by a suitable geometric primitive for instance a circle, the radius of which can, e.g., be tuned to the structure S1 using the mouse's scroll wheel control. Other examples envisaged are delineation by interactively positioning and/or stretching the geometric primitive (eg, an ellipse). Alternatively or in addition, user interaction can be kept to a minimum by using a seed-point based "zero-click" auto-contour generation provided by a "live-segmentation" requiring no additional user interaction or efforts as disclosed in Applicant's WO 2013/035026. In alternative embodiments, the specification is supplied without user input by an automatic protocol or similar. The proposed system allows in one embodiment a detailed morphology input specification to be used for the subsequent retrieval operation. The user may define morphology in terms of any one or a combination of: size specification, contour specification, edge quality (eg, roughness and/or regularity). The morphology specification as envisaged herein allows the user to effectively select the search/optimization algorithm/similarity measure to be used in the retrieval operation. The system also envisages in one embodiment the option for the user to specify qualitatively a structure property such as "cluster of micro-calcification" to name but one example. This qualitative selection may then prompt the system to select from a library or pre-stored algorithms one that is capable of searching for (in the topological sense) "not unconnected", that is, distributed structures.

Instead of or in addition to a morphology based specification, the structure property specification part of the dual specification can be realized by a multitude of different data items, all of which are envisaged herein in any combination. For instance, the input specifies a tissue composition of interest (e.g., cyst, solid lesion, glandular tissue, etc). This tissue type information can be exploited especially when at least the initial IG1 and preferably also the target image IG2 are spectral (X-ray) images acquired with an energy resolving photon-counting detector for instance. Alternatively, spectral imaging capability can be achieved by acquisition of multiple exposures by an energy integrating detector whilst switching the tube voltage sequentially to different voltage levels. In either case, in spectral images each element pixel is associated with a data structure (a vector) that represents the spectrum of the X-ray that was seen by said pixel. Spectral imagery can be implemented as a "data cube".

The structure property of interest for the corresponding structure S2 to be found can be supplied interactively by the user during display of the initial image IG1 by a suitable annotation tool. Alternatively, the specification of the structure of interest may be stored in a description language (such as XML or similar) and is then input automatically once the user has specified the location in IG1.

At step S220 the so supplied combo input specification is then used to identify a second structure S2 in the target image IG2. According to one embodiment the identification operation at step S220 comprises propagating the initially specified information across some or each of the slices in target image volume IG2 to define search regions in each slice which are then examined in more detail as will be explained below. Propagation or "transfer" of the image structure delineation can be done as for instance in previously referenced WO 2013/035026.

According to one embodiment the identification operation at step S220 is based on evaluation of a similarity measure. More particularly, the ROI propagated from the initial image into the slices of the tomosynthesis volume is compared against the initial structure of interest S1 in the initial image IG1 using said similarity measure.

The output of the identification operation at step S220 includes in particular a location within the second image and/or shape or spatial extent of the identified image structure S2 in the second image IG2.

At step S230, the slice with a similarity score or value higher than a certain threshold is returned and displayed in the view port possibly together with the initial image. In one embodiment, the slice with the region of interest S2 returning said highest similarity measure is displayed in the display device MT. In one embodiment, the so identified target slice can be displayed alongside or instead of the initial image. Preferably both images, that is the initial image and the slice with the region having the highest significance measure is displayed in the two-pane view viewport.

A number of different similarity or significance measures for the identification Step S220 are envisaged herein. The envisaged significant/similarity measures include the following or any combination of:

Similarity in entropy/texture: in the image area of the ROI (possibly including an additional clearance ("rim") for background) the entropy of a local gray-value histogram is computed. The entropy provides a measure of the information content of the image patch as per the ROI. The entropy computed this way has been observed to be small for homogeneous areas and large for heterogeneous patches including high-contrast structures. The slice whose histogram most closely resembles the local histogram in the initial image is then selected. Closeness can be measured by a suitable metric, e.g. least squares.

Gradient significance: In some or each slice on the target image IG2, an image gradient is computed and integrated along the (propagated) contour of the ROI provided by the user. The slice with the highest gradient (or with a gradient higher than a user-adjustable sufficiency threshold) along the respective propagated ROI contour is selected.

Similarity in statistical correlation: in each slice the statistical correlation of the propagated ROI with the user selected ROI of the 2D overview image is computed. The slice in IG2 with highest or sufficiently high (measured against user-adjustable sufficiency threshold) correlation with the user specified ROI in IG1 is selected.

Spectral similarity: If spectral information is available, it can be used to compute the local tissue composition to then select an ROI in IG2 with tissue composition sufficiently similar (again a sufficiency threshold may be used to quantify the similarity) to the requested tissue type (cyst, solid, etc.). A least square sum of the spectral difference can be used to establish a metric for spectral similarity for instance.

Template matching similarity: the user input specification may include selecting a structure model item from a list of structures (round lesion, spiculated mass, calcification, rib, vertebra, clavicle, etc.). The slice whose propagated structure best fits the selected model of this structure is selected.

It will be understood from the above that the propagated region(s) of interest define one or more search regions in the respective slices of the target volume IG2 for evaluation of the similarity measure. The measure may then not need to be evaluated for all pixel/voxels in each slice but evaluation is restricted to pixel or voxel information within the confines of the respective regions of interest.

It is also envisaged herein that the identification Step S220 includes an automatic or user controlled selection of a suitable significant measure or similarity measure and a suitable optimization or solution algorithm. The selection is based on the user provided input specification in particular the structural information but may alternatively be specifically selected by the user. The user may specify in drop-down menu or other input means the similarity measure to be used and/or a numerical optimizing scheme (eg, least-squares, maximum likelihood, conjugate gradients, Newton Raphson, etc) to be used for evaluating the images against the selected measure. It is envisaged herein that the system retrieves a suitable algorithm based on a suitable similarity measure pre-stored in a library or similar memory structure. In this embodiment the user indirectly determines the selection of the underlying similarity measure or algorithm to be used by providing the structure property in the input information received at Step S210. As mentioned earlier, the specification of the structure property can be achieved by for instance selection from a drop-down menu or similar graphical widget. The system then associates a corresponding tag with the specification and then uses this tag in a look-up operation to retrieve a suitable algorithm from the library of algorithm modules.

It will also be understood that any combination of a plurality (e.g., all) of the above mentioned similarity measures are also envisaged herein. For instance, a consolidated significance measure can be formed by evaluating for each of the plurality of measures and then assigning a score to an image structure by computing a weighted sum from the computed significance/similarity measures. In one embodiment, the similarity measure is only morphology based, preferably for the case when initial and target image both encode the same view on the object.

According to one embodiment there is an optional step of computing a common structure property from the respective image structure in the initial image and the corresponding structure found by the retrieval step S220 in the target image.

This can be done in one embodiment by fitting a generic model to the structures so as to explain the two structures as features of this model. For instance, in one embodiment a geometric primitive such as an ellipsoid (eg, for the mammography embodiment) or any other suitable generic feature can be fitted for shape. From the so fitted optimal model one can then compute parameters such as volume, and/or, if spectral information is being taken into consideration, water content, material composition etc. The parameters so derived may then be each displayed in an information box in numerical or graphical form for the user in the display unit, for instance overlaid on either one (or both) of the initial image or the returned slab having the identified corresponding structure S2 in it. In some, but not necessarily in all embodiments, the common property is computed from the similarity measure used for identifying the structure in the target image or the common property is at least derivable from the similarity measure. Using the common model fitted to the two corresponding structures S1,S2 allows deriving other common properties, such as a size, eg diameter of the structures. In other words, rather than merely finding the corresponding structure S2 in IG2, it is proposed herein to additionally utilize the corresponding structures S1,S2 together for computing (in one embodiment via the commonly fitted model) clinically relevant information to answer questions like: what is the size of the structure?, what is the tissue type (cyst or tumor)?, what is the composition of the structure in terms of, say, water and/or lipid content?, etc.

Reference is now made to the flow chart in FIG. 3 where an image processing method according to a second embodiment is shown. Similar as in FIG. 2, in FIG. 3, one portion, row B) that is, shows the flow chart in terms of steps whereas another portion, row A), shows illustrative imagery associable with the respective method steps in row B.

In an optional step, S305, the initial image IG1 is displayed on the display unit.

Similar to FIG. 2 above, at step S310 an input specification is received that specifies both a location and the structural property of the image structure S1 of interest in the initial image IG1. The initial image is either 2D or 3D and the target image in which the corresponding structure S2 is to be found can be likewise 2D or 3D. See illustration 1 in row A) of FIG. 3.

If the initial image IG1 is a 2D synthetic mammogram taken from a tomosynthesis volume as per a certain view (CC or MLO or other), there is an optional step S320 where the user selection in the synthetic mammogram as per step S310 is resolved into a corresponding slab in this tomosynthesis volume. Indeed, in this embodiment, step S320 for finding position and/or "thickness" of the corresponding slab (which includes the identified lesion S1 in the reconstructed tomosynthesis stack) can be implemented as described above in the embodiment of FIG. 2 for the case where initial input image is 2D and the target volume is 3D. The resolved for "position" represents for instance the center (x,y,z) of the structure S2 in the image IG2 whereas "thickness" relates to the spatial extent of said structure S2 in z-direction and hence the required slab thickness in volume image IG2 to fully cover the structure S2. See illustration 2 in row A) of FIG. 3 where the curve shown is a sketch of a similarity measure versus slice position. More particularly, the similarity measure is evaluated at the structure S1 propagated through different slices of the volume IG1. The slice position which includes the propagated structure of highest similarity is returned which is then expanded into a slab of the required thickness.

However, this "translation" step S320 from synthetic mammogram into its tomosynthesis volume is optional: For instance when initial image IG1 is a tomosynthesis volume, the selection at step S310 can be formed direct in said volume.

Once the specification (position+ additional structural information) of the initial structure S1 in initial image IG1 is gotten, the method proceeds to step S330 where the corresponding image structure is then identified in the target volume IG2. According to one embodiment this step S330 comprises the following sub-steps:

In step S330a, a search region ROI2 in the ipsilateral (second) tomosynthesis volume IG2 is defined based on the location of the initial structure S1 in IG1 and a ROI1 around this location of S1. For instance, the user can annotate a circular region around S1. Definition of search regions in the target image IG2 can then be implemented by means of "breast coordinate system" as described in Applicant's text WO2014/206881. In other words, a generic 3D representation of the object of interest (e.g., female breast or parts thereof) is used to map structures spatially from one image volume to the other. See illustration 3 in row A). Such a 3D representation can for example be established with a coordinate system, which is defined by the distance of each position in the breast with respect to suitable landmarks such as the pectoralis and the mammilla, respectively. Alternatively, the breast coordinate system is established by fitting a super-ellipsoid model to the breast contour, see Kutra et al., "An anatomically oriented breast model for MRI", Proceedings of SPIE Medical Imaging, 2015. Illustration 3 in row A) of FIG. 3 shows schematically the breast coordinate system overlaid. The system of lines represent (in CC view) the distance to the mammilla and the pectoralis (which corresponds to the left edge of illustration 3). The curved lines represent the locus of equidistant points from the mammilla and the vertical (straight) lines equidistant points from the pectoralis. The search region (shown as circle) may for example be defined (eg, centered) at the intersection of the straight and curved lines. The search region outline and the locus curved are shown merely for illustration but embodiments where the search region and/or the mentioned coordinate system lines are displayed as overlay graphics on the respect image IG1 or IG2 is envisaged herein.

In step S330b a material decomposition is computed, respectively, in the ROI around S1 in image IG1 and in the one or more search regions in IG2 by using for example a spectral look-up table. See R Alvarez et al "Energy-selective reconstruction in X-ray Computerized Tomography" in Phys Med Biol, Vol 21, No 5, pp 733-744 (1976) for details on spectral decomposition. More precisely, a spectral material decomposition into two basis materials, such as Aluminum (Al) and Poly-ethylene (PE) (to name but one pair of materials of interest for the sake of illustration only), is computed separately in the ROI around S1 and in each search region in IG2. Under the hypothesis that S1 depicts the same structure as the search region in IG2, it can be expected that the integral values of the Al and PE compartments over the ROI of structure S1 is most similar to the respective integral values in the search region in IG2, if the search region does contain the same target structure. This step 330b allows making explicit use of the spectral information for retrieving in step 330c for the corresponding structure S2 in the target image (eg, ipsilateral volume) IG2.

In step 330c, the corresponding lesion ROI S2 in the second tomosynthesis volume IG2 is identified based on suitable similarity measure as discussed above in FIG. 2, e.g. similarity of the spectral tissue composition in the first volume IG1 and second tomosynthesis volume IG2 (see illustration 4 in row A) as computed in step S330b. The spectral information or other similarity measure is then evaluated in the search region in target image IG2 and the ROI around S1 in initial image IG1. The spectral information has been shown to be a useful similarity measure which is invariant to changes experienced by the breast B in between the image acquisitions of the initial image IG1 and the target image IG2. For instance, even though the object B's position has been changed or is subject to different compression, shearing, etc, the material decomposition can be expected to remain the same. Also, as in the mammography embodiment, using a robust or invariant measure such as the spectral information based similarity measure (other invariant measures also envisaged for use herein) for image structure retrieval allows to address the fact that sometimes (as in mammography), the initial IG1 and target IG2 image have been acquired at different views (eg, MLO and CC). Although the two structures S1, S2 may have a different morphology as per differences in the two images IG1, IG2, respectively, but retrieval based on spectral information may still help lay bare their correspondence under the assumption that both images capture the same object. A purely morphology based retrieval is likely to fail in this context where object changes occurred in between acquisition of the initial IG1 and target image IG2. It will be noted that the situation is easier in the FIG. 2 embodiment, where the two images IG1 (synthetic mammogram) and the corresponding tomosynthesis block IG2 each encode image information at essentially the same view. In FIG. 2 therefore a purely morphology based similarity measure may be sufficient although this does not exclude to still use the spectral data (if available) as an additional or alternative similarity measure and such an embodiment is also envisaged herein. In one embodiment, any of the similarity measures (as listed above in connection with FIG. 2) may be used in combination with the spectral data based similarity measure. For example a morphology based similarity measure may be combined with the spectral similarity measure (for instance by forming a weighted sum) may be used in steps S330b and S330c.

The so identified structure S2, that is, its position within the volume, and depth within the respective slab is then available for further processing such as storage or display, etc.

For instance, in step S340 the identified image structure S2 in the second image volume is then displayed either in a synthetic mammogram or by displaying the corresponding slab from the volume. Displaying of the found structure S2 includes in one embodiment displaying a marker (contour outlining, highlighting or other suitable shape-or colorcoded rendering) of the identified lesion S2 in the second tomosynthesis volume IG2 and/or in the second synthetic mammogram (derived from ipsilateral volume IG2). For precise definition of the marker (e.g. contouring), a segmentation operation may be necessary.

In another embodiment, the system includes a navigation tool where the location of the identified structure S2 in IG2 with respect to the currently displayed slice within the tomosynthesis volume stack is displayed together in a breast pictogram or any other suitable graphical widget. In one embodiment, as the user changes the structure S1, for example by moving the mouse pointer, the identified structure S2 in IG2 will vary in concert, and the pictogram is updated accordingly. In this way, the user can easily assess the relative location of different structures within the target image IG2.

Optionally, there is an analyzer step S350 (the order of steps S340 and S350 are interchangeable) where a common structure property for both structures is computed. According to one embodiment the analyzer step at S350 comprises the following sub-steps:

In step S350a, a manual or automatic segmentation of the corresponding lesion ROIs S1 and S2 in their respective first IG1 and second IG2 tomosynthesis volumes is carried out. An implementation example is based on Applicant's seedpoint based live wire segmentation referenced above.

In step S350b, lesion properties are derived, preferably (but not necessarily) automatically. Such properties include volume, spectral composition (adipose/glandular volume), material decomposition (Al/PE or cyst/solid components) from the segmented lesion in the ROIs of the first and second tomosynthesis volume. The properties describe common features of both S1 and S2 and can be derived from a common model fitted to both structures. This allows accounting for the errors inherent in measurements taken from the structures S1,S2 directly. This inaccuracy may stem from fact that the images IG1,IG2 may not be true 3D and thus may not necessarily encode complete physical information which is the case for instance for the tomosynthesis imagery being a limited angle tomography reconstructions.

The so computed properties may then be displayed in numerical or graphical form as "info" overlays in association with the respective structures S1 or S2 in one or both images IG1,IG2.

The computation in step S350b may be based on the similarity measure computations in step S330c or as described in FIG. 2. For instance, the similarity or significance measure may need to be converted into a suitable format. In other embodiments, at least step S350b can be dispensed with and the method outputs direct, as the common lesion property, the similarity measure value as computed when identifying the structure S2 at step S330.

In the above, it may be preferable that target and initial images are spectral when spectral information is included in the input specification. But there are also embodiments envisaged where only one of the target or initial image is spectral. In this uni-laterally spectral embodiment, the system is contemplated to include suitable middleware components that translates or correlates spectral information as per one image into image contrast information of the other non-spectral image. In this manner, a cross modality search is possible where for instance the initial image is spectral X-ray but the target image is an MRI image to name but one example. One embodiment for a cross-modality search where corresponding structures are to be found is in a 3D MRI dataset versus image material from a mammography prior exam. If MRI image data is involved, the additional structure property supplied by the user at the input may comprise s specification of contrast uptake. Contrast uptake specification is also envisaged when at least one of initial and target image is an X-ray image acquired whilst contrast agent resides in the object of interest such as in angiography.

It will be appreciated that in the above described embodiments, the additional structure property may be explicitly supplied by the user as explicit input via the UI (for instance by choosing a tissue type of interest) but may also be provided implicitly. For instance, if the input and/or target images are spectral, the user input may be as simple as a location and/or ROI around the location to specify the initial structure S1 as described above. The system then automatically evaluates the spectral similarity in the target image IG2 to find S2. In this sense, the additional structure property "spectral" has been implicitly provided by specifying the S1 location in the spectral image IG1.

Although the above embodiments have been described for embodiments using absorption image modalities or MRI modalities other image modalities and any combination of modalities for the initial and/or target image are also envisaged herein such as phase-contrast or dark-field imaging.

Also, the retrieval operation has been described to extend across two (FIG. 2) or two or three (FIG. 3) images with the understanding that an arbitrary long "chain" of interconnected cross-image retrievals are also envisaged for any combination of image modalities. For instance, one starts with initial image IG1 and a structure S1 therein and the retrieval then proceeds via a chain of intermediate images and structure therein to final structure S2 in target image IG2.

Although the method and system has been explained above with particular reference to mammography applications this is not to be construed as limiting and other applications and imagery may also be suitable for application of the proposed system. For instance, application of the proposed method and system to chest imaging and related images and imagers are also envisaged herein.

The image processing system IPS may be arranged as a software module or routine with suitable interfaces (such as input port IN and output port OUT) and may be run on a general purpose computing unit or a dedicated computing unit. For instance image processing system IPS may be executed on a workstation or operator console of the imager MX. The image processing system IPS with some or all of its components may be resident on the executive agency (such as a general purpose computer, workstation or console) or may be accessed remotely/centrally by the executive agency via a suitable communication network in a distributed architecture. The components may be implemented in any suitable programming language such as C++ or others.

In one embodiment, some or all of the components of the image processing system IPS may be arranged as dedicated FPGAs (field-programmable gate array) or similar stand-alone chips.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

The invention claimed is:

1. An image processing system comprising:
   an input port configured to receive, for a first image of an object, an input specification comprising:
     a location of a first image structure in the first image, and
     a structure property that relates to a corresponding physical property of at least a part of the object, wherein the structure property specification includes at least spectral information that relates to the physical property of the at least a part of the object;
   an image structure retriever configured to identify, based on the input specification, a second image structure in a second image of the object by:
     defining a search region in the second image based on the location of the first image structure in the first image, and a region of interest around the location of the first image structure, and
     performing a material decomposition in the region of interest around the location of the first image structure and in the search region in the second image; and
   a graphics display generator configured to display on a display device the second image structure.

2. The image processing system as per claim 1, wherein the image structure retriever's identification includes comparing the search region with the region of interest based on a similarity measure.

3. The image processing system as per claim 2, wherein the similarity measure includes any one or a combination of: grey value histogram similarity, similarity in spectral or material composition, similarity in any one of size, morphology, texture, contrast uptake.

4. The image processing system as per claim 1, wherein the structure property specification includes any one or a combination of: i) a size and/or shape parameter, ii) material type.

5. The image processing system as per claim 4, wherein the image structure retriever identification includes propagating a shape from the first into the second image, the shape being specified by the shape parameter, or another shape parameter.

6. The image processing system as per claim 1, wherein object is repositioned and/or deformed between respective acquisitions by an imager of the first and second image.

7. The image processing system as per claim 1, wherein the first and the second image furnish different views of the object, the first and second image structures being representative of a part of interest of or in said object.

8. The image processing system as per claim 1, wherein the first image is a 2D or a 3D image and wherein the second image is a 2D or 3D image.

9. The image processing system as per claim 1, wherein the identification of the retriever includes identifying a shape/location of the second structure in the second image.

10. The image processing system as per claim 1, wherein the image structure retriever's identification includes identifying a search region within the second image for application of the similarity measure to image information within said search region.

11. The image processing system as per claim 1, wherein the graphics display generator is configured to effect displaying the first image structure and the second image structure together on the display device.

12. The image processing system as per claim 1, comprising a structure analyzer configured to compute a common structure property for said first and second structures.

13. The image processing system as per claim 1, including an interactive user interface operable by a user to supply said input specification whilst the first image is being displayed on the display device.

14. The image processing system as per claim 2, wherein the image structure retriever's identification includes performing an optimization or search algorithm in respect of the similarity measure, said algorithm and/or similarity measure being selected based on the received input specification.

15. An imaging arrangement including an imager and an image processing system, the image processing system comprising:
- an input port configured to receive, for a first image of an object, an input specification comprising:
  - a location of a first image structure in the first image, and
  - a structure property that relates to a corresponding physical property of at least a part of the object, wherein the structure property specification includes at least spectral information that relates to the physical property of the at least a part of the object;
- an image structure retriever configured to identify, based on the input specification, a second image structure in a second image of the same object by:
  - defining a search region in the second image based on the location of the first image structure in the first mage, and a region of interest around the location of the first image structure, and
  - preforming a material decomposition in the region of interest around the location of the first image structure and in the search region in the second image; and
- a graphics display generator configured to display on a display device the second image structure.

16. An image processing method, comprising:
for a first image of an object, receiving an input specification comprising:
- a location of a first image structure in the first image, and
- a structure property that relates to a corresponding physical property of at least a part of the object, wherein the structure property specification includes at least spectral information that relates to the physical property of the at least a part of the object;

based on said input specification, identifying a second image structure in a second image of the same object by:
- defining a search region in the second image based on the location of the first image structure in the first image, and a region of interest around the location of the first image structure, and
- performing a material decomposition in the region of interest around the location of the first image structure and in the search region in the second image; and displaying said second image structure.

17. A non-transitory computer-readable medium comprising a computer program product recorded thereon and capable of being run by a processor, including program code instructions for implementing the method of claim 16.

* * * * *